United States Patent [19]

Allison

[11] 4,397,957

[45] Aug. 9, 1983

[54] SPECIFIC-ION GAS-SENSING CARBONATE ANALYZER

[75] Inventor: Joseph L. Allison, Baton Rouge, La.

[73] Assignee: The Dow Chemical Company, Midland, Mich.

[21] Appl. No.: 351,813

[22] Filed: Feb. 24, 1982

[51] Int. Cl.$^3$ ............... G01N 27/26; G01N 27/40; G01N 27/56

[52] U.S. Cl. .................... 436/133; 436/146; 436/175; 436/181

[58] Field of Search ............ 23/230 R; 204/195 M; 436/133, 181, 175, 146

[56] References Cited

U.S. PATENT DOCUMENTS

| | | | |
|---|---|---|---|
| 3,689,222 | 9/1972 | McFarland et al. | 23/230 R |
| 3,801,281 | 4/1974 | Thompson | 436/133 X |
| 3,939,693 | 2/1976 | Dumont | 73/19 |
| 4,018,660 | 4/1977 | Hansen | 204/195 M X |
| 4,019,862 | 4/1977 | Dahms | 436/133 X |
| 4,046,510 | 9/1977 | Becker | 436/146 |
| 4,063,891 | 12/1977 | Becker | 436/146 |
| 4,196,056 | 4/1980 | Kumar | 204/195 M X |

OTHER PUBLICATIONS

H. H. Willard et al., "Advanced Quantitative Analysis," pp. 317–320, D. Van Nostrand, New York, 1943.
Chemical Abstracts, 82:67702s (1975).

*Primary Examiner*—Sidney Marantz
*Attorney, Agent, or Firm*—A. J. Young

[57] ABSTRACT

A method for determining the concentration of carbonate salts in solutions containing other inorganic salts. The method includes converting the carbonate salts to carbon dioxide by acidifying the sample, sweeping the acidified solution with an inert gas to strip the carbon dioxide from the solution and contacting an ion-selective gas-sensing electrode with the gas stream. The electrode includes a buffered solution which changes in pH depending on the concentration of carbon dioxide in the gas stream thereby providing a measure of the carbonate salt concentration in the sample.

4 Claims, No Drawings

SPECIFIC-ION GAS-SENSING CARBONATE ANALYZER

BACKGROUND OF THE INVENTION

This invention relates to a method for analyzing carbonate salts in solutions. More particularly, this invention relates to an automated quantitative determination of the concentration of carbonate salts in aqueous solutions containing a large concentration of other salts.

An inorganic salt, such as sodium chloride, is used in many manufacturing processes. Such salt is normally obtained by direct mining or from brine wells which use water to dissolve the salt in the underground formations. This salt invariably contains substantial hardness impurities such as calcium and magnesium salts which will interfere with its use in the manufacturing processes. Therefore, it is necessary to remove as much as these impurities as possible before the salt is used in a manufacturing process.

One method of removing these hardness impurities is to dissolve the salt, if it is not already in solution from a brine well, and then treat it with sodium carbonate to precipitate out the water insoluble carbonate salts of the hardness impurities. In order to insure maximum removal of the impurities, it is necessary to analyze effluent from the treatment process so that an excess of sodium carbonate is used in the process.

Known prior art methods for the determination of carbonate salts in solutions comprise acidifying a sample to be analyzed to release an equivalent amount of carbon dioxide gas and then measuring the amount of carbon dioxide gas released by titrimetry, gravimetry, or infrared spectroscopy. The titrimetric and gravimetric methods are subject to substantial error due to interference by substances which, upon acidification of the sample, form acid gases or gases which upon contact with water form acids. The infrared method requires expensive equipment, has poor sensitivity and accuracy at low carbonate concentrations, and is affected by changes in temperature and moisture content of the liberated gases.

SUMMARY

In general, the present invention provides a method for determining the concentration of carbonate salts in a solution sample, comprising the steps of (a) acidifying the sample to convert the carbonate salts to carbon dioxide; (b) sweeping the acidified solution with an inert gas, thereby stripping the carbon dioxide from the solution and forming a gas stream containing the carbon dioxide; and (c) contacting an ion-selective gas-sensing electrode with the gas stream, the electrode including a second solution which is subject to changes in pH when contacted by the gas stream containing different carbon dioxide concentrations, the electrode having an electrical output responsive to changes in pH of the second solution, whereby the electrical output of the electrode provides a measure of the concentration of carbon dioxide in the gas stream and the concentration of the carbonate salt in the sample. The ion-selective electrode may be used in conjunction with any standard reference electrode and in either a potentiometric or amperometric mode; however, a potentiometric system is preferred. As used herein, the term "carbonate" is defined and intended to include bicarbonate.

The present invention may also include a step of adding a reducing agent to the sample being analyzed before sweeping the acidified sample with an inert gas. This step is important where the sample being analyzed contains substances that will release a halogen gas when the sample is acidified. The purpose of adding the reducing agent is to prevent release of the free halogen gas into the inert gas stream, thereby preventing the halogen gas from interfering with and causing an error in the measurement made by the ion-selective electrode. For example, if hypohalites are present in the sample, acidification will convert them to the corresponding halogens, unless a reducing agent is added before adding acid. The hypohalite most commonly present is sodium hypochlorite, which on acidification in the absence of a reducing agent forms chlorine. The reducing agent may be added before, concurrently or after acid addition to the sample, but must be added before sweeping the sample with the inert gas. In the latter case, the reducing agent will reduce any liberated halogen before it can become a problem. The preferred reducing agent is hydroxylamine or hydroxylamine hydrochloride.

It is an object of this invention to provide a method for determining the concentration of salts in solutions which is inexpensive, accurate, and sensitive. It is a further object of this invention to provide a method for carbonate salt determination in solutions which is free of interference by substances which may cause substantial error in the measurement obtained. It is a further object of this invention to provide a method for carbonate determination which is particularly beneficial and adapted to the automatic quantitative determination of carbonate salts in samples of aqueous solutions. Other objects of the invention will be apparent to those skilled in the art from the more detailed description which follows.

DESCRIPTION OF THE PREFERRED EMBODIMENT

The following description illustrates the manner in which the principles of this invention are applied, but is not to be construed as in any sense limited the scope of the invention.

The method of the present invention is particularly useful for monitoring the amount of sodium carbonate needed to remove hardness impurities such as calcium and magnesium from a sodium chloride brine used in an electrolysis process to make sodium hydroxide and chlorine. In treating sodium chloride brine to remove hardness impurities, an excess of sodium carbonate must be maintained to insure satisfactory results, but the amount of excess used needs to be monitored carefully to provide good overall brine properties and for economic reasons. The concentration of excess sodium carbonate in the brine solution after treatment with sodium carbonate may range between about 0.1 and about 4 grams of sodium carbonate per liter, and more preferably, between about 0.2 and about 3 grams per liter. Beneficially, the level of hardness impurities in treated brine is maintained at or below three parts per million to provide the most satisfactory results in the electrolytic process. In order to maintain this level of hardness, it is necessary to keep the excess sodium carbonate level in the treated brine at about one and one-half grams per liter. Known methods of sampling, with subsequent analysis of the samples, are slow, inefficient and inaccurate for monitoring excess carbonate in treated brine.

The present analyzer is temperature-independent in the 0°–50° C. range, operates well with nitrogen gas saturated with water vapor, and is inexpensive. The carbon dioxide evolved and swept from solution by a stream of nitrogen gas, using standard analytical technics, is sensed by a specific-ion gas-sensing electrode manufactured by Orion Research, Inc. (Model No. 95-02). A pH meter manufactured by Brinkman Instruments, Inc. (Model No. 104) is used to measure the potential difference of the electrode before and after it is exposed to the carbon dioxide. Other equivalent specific-ion gas-sensing electrodes and pH meters, as well as other inert carrier gases such as air or helium, may of course be used.

In carrying out the preferred method of the present invention, an excess of acid and reducing agent is utilized. The amount of acid added to the sample is preferably between about two and about four times the amount required to convert all of the carbonate salts in the solution to carbon dioxide. The amount of reducing agent added is also preferably between about two and about four times the amount required to reduce any hypohalites or other halogen-producing compounds present in the sample. The concentration of sodium hypochlorite in treated brine may range from about ten to about five hundred milligrams per liter.

Preferably, the determinations are carried out continuously and automatically. A base-line determination is made before acidifying the brine sample and sweeping the acidified sample with nitrogen. For the baseline determination, the carrier stream of inert gas is sensed by the electrode. This baseline value may be automatically stored in the "memory" of a computer or microprocessor, and subsequently retrieved and subtracted from the value registered by exposing the electrode to the carrier stream enriched with carbon dioxide after a brine sample has been acidified and nitrogen-purged. The potential difference obtained thereby may be then automatically converted into the corresponding value of excess sodium carbonate in the brine sample. In addition, the response of the electrode to the change in carbon-dioxide concentration in the stream of carrier gas may be further utilized to automatically control the quantity of sodium carbonate being added to a brine stream in a brine-treatment process.

The invention will now be illustrated by means of the following example.

EXAMPLE 1

Brine samples that had been treated with solutions of sodium carbonate were analyzed by the method of the present invention, as described hereinabove. The results thereby obtained are listed in Table I, below.

TABLE I

| EXCESS $Na_2CO_3$ (Grams/Liter) | BASELINE RESPONSE (Milivolts) | SAMPLE RESPONSE (Milivolts) | POTENTIAL DIFFERENCE (Milivolts) |
|---|---|---|---|
| 2.5 | 5780 | 4242 | 1538 |
| 2.5 | 5780 | 4230 | 1550 |
| 2.5 | 5780 | 4217 | 1563 |
| 2.5 | 5780 | 4220 | 1560 |
| 2.5 | 5780 | 4223 | 1557 |
| 2.5 | 5780 | 4219 | 1561 |
| — | — | — | — |
| 2.0 | 5780 | 4341 | 1439 |
| 2.0 | 5780 | 4336 | 1444 |
| 2.0 | 5780 | 4337 | 1443 |
| 2.0 | 5780 | 4319 | 1461 |
| — | — | — | — |
| 1.54 | 5780 | 4463 | 1317 |
| 1.54 | 5780 | 4458 | 1322 |
| 1.54 | 5780 | 4433 | 1347 |
| 1.54 | 5780 | 4425 | 1355 |
| — | — | — | — |
| 1.24 | 5780 | 4568 | 1212 |
| 1.24 | 5780 | 4545 | 1235 |
| 1.24 | 5780 | 4519 | 1261 |
| 1.24 | 5780 | 4525 | 1255 |
| 1.24 | 5780 | 4523 | 1257 |
| — | — | — | — |
| 0.968 | 5780 | 4648 | 1132 |
| 0.968 | 5780 | 4683 | 1097 |
| 0.968 | 5780 | 4676 | 1104 |
| 0.968 | 5780 | 4668 | 1112 |
| — | — | — | — |
| 0.70 | 5780 | 4830 | 950 |
| 0.70 | 5780 | 4832 | 948 |
| 0.70 | 5780 | 4837 | 943 |
| — | — | — | — |
| 0.47 | 5780 | 5095 | 685 |
| 0.47 | 5780 | 5078 | 702 |
| — | — | — | — |
| 0.306 | 5780 | 5328 | 452 |
| 0.306 | 5780 | 5331 | 449 |
| 0.306 | 5780 | 5338 | 442 |
| — | — | — | — |
| 0.128 | 5780 | 5613 | 167 |
| 0.128 | 5780 | 5619 | 161 |
| 0.128 | 5780 | 5615 | 165 |
| — | — | — | — |

While certain representative embodiments and details have been shown for the purpose of illustrating this invention, it will be apparent to those skilled in the art that various changes and modifications can be made therein without departing from the spirit and scope of the invention. For example, the present method may be used to monitor carbonate salts in solutions used for purposes other than herein described.

What is claimed is:

1. A method for determining the concentration of a carbonate salt in a solution sample, comprising the steps of:
   (a) acidifying the sample to convert the carbonate salt to carbon dioxide;
   (b) sweeping the acidified solution with an inert gas, thereby stripping the carbon dioxide from the solution and forming a gas stream containing the carbon dioxide; and
   (c) contacting an ion-selective gas-sensing electrode with the gas stream, the electrode including a second solution which is subject to changes in pH when contacted by the gas stream containing different carbon dioxide concentrations, the electrode having an electrical output responsive to the changes in pH of the second solution, whereby the electrical output of the electrode provides a measure of the concentration of the carbon dioxide in the gas stream and the concentration of the carbonate salt in the sample.

2. The method of claim 1, wherein a reducing agent, in sufficient quantity, is added to the sample before sweeping the acidified sample with an inert gas, thereby preventing substances in the sample which will release halogen gases upon acidification from releasing the same.

3. The method of claim 2, wherein the reducing agent is hydroxylamine or hydroxylamine hydrochloride.

4. The method of claim 3, wherein the sample is a solution of sodium chloride brine and the carbonate salt is sodium carbonate.

* * * * *